(12) United States Patent
Kolter et al.

(10) Patent No.: US 8,715,729 B2
(45) Date of Patent: May 6, 2014

(54) RAPIDLY DISINTEGRATING, SOLID COATED DOSAGE FORM

(75) Inventors: Karl Kolter, Limburgerhof (DE); Silke Gebert, Grünstadt (DE); Yoshitaka Katsuno, Shanghai (CN)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/331,439

(22) Filed: Dec. 20, 2011

(65) Prior Publication Data

US 2012/0164223 A1 Jun. 28, 2012

Related U.S. Application Data

(60) Provisional application No. 61/425,789, filed on Dec. 22, 2010.

(51) Int. Cl.
*A61K 9/28* (2006.01)
*A61K 9/20* (2006.01)
*A61K 9/32* (2006.01)

(52) U.S. Cl.
USPC .......................... 424/474; 424/464; 424/482

(58) Field of Classification Search
None
See application file for complete search history.

(56) References Cited

U.S. PATENT DOCUMENTS

| | | | |
|---|---|---|---|
| 6,579,953 B1 | 6/2003 | Gotsche et al. | |
| 6,696,085 B2 | 2/2004 | Rault et al. | |
| 7,118,765 B2 | 10/2006 | Norman et al. | |
| 8,071,128 B2 * | 12/2011 | Ohta et al. | 424/464 |
| 2002/0071864 A1 | 6/2002 | Kim et al. | |
| 2005/0107498 A1 | 5/2005 | Kolter et al. | |
| 2008/0044469 A1 | 2/2008 | Kolter et al. | |
| 2010/0173859 A1 | 7/2010 | Kolter et al. | |
| 2010/0178349 A1 * | 7/2010 | Kolter et al. | 424/489 |
| 2011/0142888 A1 | 6/2011 | Cech et al. | |
| 2012/0053248 A1 | 3/2012 | Kolter et al. | |
| 2012/0076858 A1 | 3/2012 | Kolter et al. | |
| 2012/0202894 A1 | 8/2012 | Kolter et al. | |
| 2012/0244197 A1 | 9/2012 | Djuric et al. | |

FOREIGN PATENT DOCUMENTS

| | | |
|---|---|---|
| CA | 2517372 A1 | 9/2004 |
| DE | 1077430 B | 3/1960 |
| DE | 1081229 B | 5/1960 |
| DE | 1094457 B | 12/1960 |
| DE | 102004031835 A1 | 1/2006 |
| EP | 0839526 A2 | 5/1998 |
| EP | 1523974 A1 | 4/2005 |
| EP | 2106789 A1 | 10/2009 |
| GB | 922457 A | 4/1963 |
| GB | 922458 A | 4/1963 |
| GB | 922459 A | 4/1963 |
| JP | 2004-265216 A | 9/2004 |
| WO | WO-00/18375 A1 | 4/2000 |
| WO | WO-0018375 A1 | 4/2000 |
| WO | WO-01/04195 A1 | 1/2001 |
| WO | WO-03/051338 A1 | 6/2003 |
| WO | WO-03/070224 A1 | 8/2003 |
| WO | WO-03070224 A1 | 8/2003 |
| WO | WO-2004075828 A2 | 9/2004 |
| WO | WO-2006/002808 A2 | 1/2006 |
| WO | WO-2007/071581 A2 | 6/2007 |
| WO | WO-2008/148731 A1 | 12/2008 |
| WO | WO-2008/148733 A2 | 12/2008 |
| WO | WO-2008148742 A2 | 12/2008 |
| WO | WO-2010/069795 A2 | 6/2010 |

OTHER PUBLICATIONS

International Search Report of PCT/EP2011/073531 date of mailing Jun. 15, 2012.
Trockene Granulation, "Die Tablette", W. Ritschel und A. Bauer-Brandl, 2. Auflage 2002 Editio Cantor Verland Aulendort.
Guidance for Industry, Orally Disintegrating Tables, U.S. Department of Health and Human Services Food and Drug Administration, Apr. 2007.
Volker Buhler, Springer Verlag Berlin Heidelberg 2005 Gerneral notes on Synthesis and Soluble polyvinylpyrrolidone.
Bühler, "Polyvinylpyrrolidone Excipients for Pharmaceuticals", pp. 214-216, (2005).
International Search Report for PCT/EP2010/069556.

\* cited by examiner

*Primary Examiner* — David J Blanchard
*Assistant Examiner* — Tigabu Kassa
(74) *Attorney, Agent, or Firm* — Novak Druce Connolly Bove + Quigg LLP

(57) ABSTRACT

Rapidly disintegrating, solid coated dosage form comprising a solid core consisting of at least 60% by weight of an auxiliary mixture, up to 40% by weight of at least one active ingredient, and optionally further auxiliaries, coated with at least one film coating comprising completely or partially hydrolyzed, rapidly water-soluble polyether-vinyl ester graft polymers, methods for the production thereof, and their use.

20 Claims, No Drawings

RAPIDLY DISINTEGRATING, SOLID COATED DOSAGE FORM

CROSS-REFERENCE TO RELATED APPLICATIONS

This application claims benefit under 35 U.S.C. §119(e) of U.S. Provisional Patent App. Ser. No. 61/425,789, filed Dec. 22, 2010, which is incorporated herein by reference in its entirety.

The present invention relates to rapidly disintegrating, solid coated dosage forms, where the solid dosage form comprising a solid core, obtained using a pharmaceutical composition in the from of agglomerates comprising sugars or sugar alcohols, disintegrants and water-insoluble polymers, coated with at least one rapidly water-soluble film coating, comprising graft polymer of polyether and vinyl acetate, where the vinyl acetate has been completely or partially hydrolyzed after the polymerization.

Solid dosage forms which rapidly disintegrate and/or rapidly dissolve in the mouth, such as tablets, are achieving ever greater importance for the oral application of drugs. Such tablets have to disintegrate within a short time, at best within 30 seconds, within the oral cavity, have a pleasant flavor and must not leave behind a sandy feel. Similarly, they should be easy to produce, with direct tableting offering considerable advantages over wet granulation. In addition, they should have high mechanical strength so that they withstand packaging procedures, transportation and also the squeezing out from packagings in an undamaged manner. Besides tablets, however, other solid dosage forms such as granules, pellets or extrudates are also of interest. Thus, finely divided dosage forms such as granules can be packaged, for example, in sachets or in capsules.

Such tablets are usually manufactured and administered without any film coating. The reason for this is in particular the very short disintegration time in water, especially small amounts of water as for example in the mouth, which is required by such tablets. According to the definition of the US authorities for tablets that disintegrate rapidly in the mouth ("Guidance for Industry—Orally disintegrating tablets", USA, dated Mar. 22, 2007) it is required that such tablets disintegrate in the mouth within 30 seconds without chewing or drinking liquid.

Solid administration forms such as tablets are provided with a coating for a very wide variety of reasons. Thus, for example, the appearance, the distinguishability and swallowability can be improved, and a bitter flavor can be concealed. The administration form can be protected against external influences such as, for example, moisture or oxygen, for example during storage and transportation.

Secondly, by using white and/or colored pigments, they can conceal the underlying core and thus provide a uniform colored appearance. A colored film coating likewise serves as color coding so as not to mix up solid dosage forms of the same shape that contain different active ingredients. Such a coating should in principle be as uniform, smooth and shiny as possible and must not be adhesive. Film coatings are therefore an important member of the formulation of a solid dosage form.

Coated, orally rapidly disintegrating tablets are hitherto not known. Nevertheless, the use of film coatings also for orally rapidly disintegrating solid dosage forms would be desirable. The difficulty when producing such forms lies in that an extremely moisture-sensitive core has to be sprayed with an aqueous spray suspension and must not swell, disintegrate or be damaged in some other way in the process. Moreover, the film coating must dissolve in the mouth upon contact with saliva within a few seconds so that the entire disintegration of the film tablet is completed within 60 seconds or preferably within 30 seconds or less, as is required for such dosage forms.

The person skilled in the art would therefore expect that a tablet core which has such a rapid disintegration time cannot be coated by aqueous means.

It would likewise be expected that the disintegration time of a coated tablet is extended at least by the dissolution time of the film coating since it is only then that the core comes into contact with water and can start to disintegrate. Such a coating would consequently hinder the attainment of the required short disintegration times.

Orally rapidly disintegrating tablets often consist of sugars and sugar alcohols, effervescent systems, microcrystalline cellulose and other water-insoluble fillers such as calcium hydrogenphosphate, cellulose derivatives, corn starch or polypeptides. Furthermore, water-soluble polymers are used as binders, customary disintegrants (such as crospovidone, sodium and potassium salts of crosslinked carboxymethylcellulose, sodium salt of carboxymethyl starch, low-substituted hydroxypropylcellulose L-HPC) and essentially inorganic water-insoluble constituents (silicas, silicates, inorganic pigments). Furthermore, the tablets can also comprise surfactants.

WO 2003/051338 describes a directly tabletable and readily compressible auxiliary formulation which comprises mannitol and sorbitol. Firstly, an auxiliary premix is prepared by dissolving mannitol and sorbitol in water and subsequently spray-drying (customary spray-drying and SBD methods). Mannitol can then be additionally added to this coprocessed mixture. Tablets which additionally comprise disintegrants, release agents, pigments and an active ingredient reportedly disintegrate in the oral cavity within 60 seconds.

US 2002/0071864 A1 describes a tablet which disintegrates in the oral cavity within 60 seconds and is primarily formulated from a physical mixture of spray-dried mannitol and a coarsely granular crosslinked polyvinylpyrrolidone and also a limited selection of active ingredients. These tablets have a breaking strength of ca. 40 N and produce an unpleasant, sandy mouth feel.

According to U.S. Pat. No. 6,696,085 B2, a methacrylic acid copolymer type C should be used as disintegrant. The methacrylic acid copolymer type C is an enteric polymer which is not soluble in the acidic pH range, but is water-soluble in the pH range of 7, as is present in the oral cavity. Besides a low breaking strength (less than 20 N), the tablets have a high friability (more than 7%) and, with about 15% by weight, include a relatively high fraction of a coarsely particulate disintegrant. They have low mechanical strength and, on account of the high proportion of coarsely particulate disintegrant, have an unpleasant sandy mouth feel.

EP 0839526 A2 describes a pharmaceutical administration form consisting of an active ingredient, erythritol, crystalline cellulose and a disintegrant. Furthermore, mannitol is incorporated and the disintegrant used is crosslinked polyvinylpyrrolidone, thus giving a physical mixture of the feed materials. The tablets reportedly disintegrate in the oral cavity within 60 seconds.

The application JP 2004-265216 describes a tablet which disintegrates in the mouth within 60 seconds and consists of an active ingredient, a water-soluble polyvinyl alcohol-polyethylene glycol copolymer as binder, sugar/sugar alcohol and disintegrant.

The use of polyvinyl alcohol-polyether graft copolymers as coatings or binders in pharmaceutical administration forms or as packaging material or as additive in cosmetic, dermatological or hygiene preparations is known, for example, from WO 00/18375. First, for example, a formulation for a film coating is described which consists of a polyvinyl alcohol-polyether graft copolymer and the customary coating constituents for coloring and covering, namely iron oxide, talc and titanium dioxide.

WO 03/070224 describes coatings which consist of polyvinyl alcohol-polyether graft copolymers, a component with hydroxyl, amide or ester functions and further customary coating constituents. Here, firstly a premix of the feed materials is prepared as a physical mixture, which is then dispersed in water.

WO 2006/002808 discloses a rapidly dispersible, finely divided pulverulent film coating that does not have a separation tendency and is based on polyvinyl alcohol graft polymers with particular stability and particularly low roughness.

WO 2010/069795 discloses a pharmaceutical composition provided with a film coating and comprising a specific active ingredient and at least one disintegrant selected from the group comprising crospovidone, croscarmellose-sodium, sodium starch glycolate, low-substituted hydroxypropylcellulose, Ludiflash® or combinations thereof, and also further pharmaceutically acceptable auxiliaries in order to obtain a rapidly disintegrating tablet. All substances known to the person skilled in the art for such purposes should be able to be used as film coating suitable compositions. The only substance specifically mentioned and used in the examples is "Opadry pink film coat". The disintegration time of the coated tablets from example 1, 6, 7 and 12 were ascertained in the USP disintegration testing device and were 69 to 140 seconds for a tablet size of 125 to 500 mg.

It was an object of the present invention to provide orally rapidly disintegrating, solid coated dosage forms such as, in particular, tablets, which, despite the film coating, nevertheless have a short disintegration time of less than 60 seconds tested in accordance with USP, and also maximum 45 seconds and less in the case of disintegration in the mouth.

Accordingly, a rapidly disintegrating, solid coated dosage form has been found. Preferably, all embodiments are an orally rapidly disintegrating, solid coated dosage form. In particular, a rapidly disintegrating, solid coated dosage form comprising a solid core consisting of components A), B) and D) coated with at least one film coating C) has been found, where A) is at least 60% by weight of an auxiliary mixture consisting of
  a) 60 to 97% by weight of at least one sugar or sugar alcohol,
  b) 1 to 25% by weight of disintegrant
  c) 0 to 30% by weight of at least one film-forming polymer,
  d) 0 to 15% by weight of at least one water-soluble polymer,
  e) 0 to 15% by weight of further, customary auxiliaries,
    where the constituents a) to e) add up to 100% by weight,
B) is up to 40% by weight of at least one active ingredient,
C) is a film coating consisting of
  f) 20 to 70% by weight of a rapidly water-soluble polyether-vinyl ester graft polymer of polyether and vinyl ester, where the polymerized vinyl esters have been completely or partially hydrolyzed,
  g) 0 to 70% by weight of at least one pigment,
  h) 0 to 30% by weight of a finely divided crospovidone with an average particle diameter between 2 and 30 micrometers, and
  i) 0 to 30% by weight of further customary auxiliaries,
    where the constituents f) to i) add up to 100% by weight, and
D) is 0-15% by weight of further customary auxiliaries,
where the components A) plus B) plus D) add up to 100% by weight,
having a disintegration time of at most 45 seconds.

In one particularly preferred embodiment, the film-forming constituent f) is a rapidly water-soluble polyethylene glycol-vinyl acetate graft polymer, where the polymerized vinyl acetate has been hydrolyzed to more than 90 percent and the fraction of polyvinyl alcohol/vinyl acetate is 70 to 80% by weight and the fraction of polyethylene glycol is 20 to 30% by weight.

A one preferred embodiment, the disintegrant b) is selected from the group consisting of crospovidone, croscarmellose, sodium or calcium carboxymethyl starch and L-hydroxypropylcellulose. The particularly preferred disintegrant b) is a crospovidone. A particularly preferred disintegrant b) is a finely divided crospovidone with an average particle diameter between 2 and 30 micrometers. Very particular preference is given to a finely divided crospovidone with an average particle diameter between 2 and 30 micrometers and a hydration capacity of more than 7 g/g. The hydration capacity is determined at 23° C. according to the following method: 2 g of polymer are weighed into a centrifuge tube and left to swell with 40 ml of water for 15 minutes. The mixture is then centrifuged for 15 minutes at 2000 rpm, the supernatant liquid is poured off and the sample is weighed again.

$$\text{Hydration capacity} = \frac{\text{final weight} - \text{tare}}{\text{initial weight}}$$

(see also V. Buehler, "Polyvinylpyrrolidone Excipients for Pharmaceuticals", p. 132 ff., Springer Verlag Berlin Heidelberg, 2005)

In a further preferred embodiment, the fraction of pigment g) in the solid film coating C) is at least 40 percent by weight.

A further preferred embodiment is a rapidly disintegrating, solid coated dosage form—in particular in the form of tablets—comprising a solid core consisting of the components A), B) and D) coated with at least one film coating C), where
A) is at least 60% by weight of an auxiliary mixture consisting of
  a) 60 to 97% by weight of at least one sugar or sugar alcohol,
  b) 1 to 25% by weight of at least one disintegrant selected from the group consisting of crospovidone, croscarmellose, sodium of calcium carboxymethyl starch and L-hydroxypropylcellulose,
  c) 1-15% by weight of at least one water-insoluble, film-forming polymer,
  d) 0 to 15% by weight of at least one water-soluble polymer,
  e) 0 to 15% by weight of further, customary auxiliaries,
    where the constituents a) to e) add up to 100% by weight,
B) is up to 40% by weight of at least one active ingredient,
C) is a film coating consisting of
  f) 20 to 70% by weight of a rapidly water-soluble polyether-vinyl ester graft polymer of polyether and vinyl ester, where the polymerized vinyl esters have been completely or partially hydrolyzed, g) 0 to 70% by weight of at least one pigment,
h) 0 to 30% by weight of a finely divided crospovidone with an average particle diameter between 2 and 30 micrometers, and
i) 0 to 30% by weight of further customary auxiliaries, where the constituents f) to i) add up to 100% by weight, and D) is 0-15% by weight of further customary auxiliaries, where the components A) plus B) plus D) add up to 100% by weight, having a disintegration time of at most 45 seconds.

A further preferred embodiment is a rapidly disintegrating, solid coated dosage form—in particular in the form of tablets—comprising a solid core consisting of the components A), B) and D) coated with at least one film coating C), where
A) is at least 60% by weight of an auxiliary mixture consisting of
 a) 75 to 95% by weight of mannitol or erythritol or of a mixture thereof,
 b) 3 to 15% by weight of crospovidone with an average particle size of from 2 to 30 micrometers and a hydration capacity of at least 7 g/g,
 c) 2 to 10% by weight of polyvinyl acetate,
 d) 0.01 to 2% by weight of at least one water-soluble polymer, and
 e) 0.001 to 2% by weight of further, pharmaceutically customary auxiliaries, where the constituents a) to e) add up to 100% by weight,
B) is up to 40% by weight of at least one active ingredient,
C) is a film coating consisting of
 f) 20 to 70% by weight of a rapidly water-soluble polyalkylene glycol-vinyl ester graft polymer of polyalkylene glycol and vinyl ester, where the polymerized vinyl esters have been completely or partially hydrolyzed,
 g) 0 to 70% by weight of at least one pigment,
 h) 0 to 30% by weight of a finely divided crospovidone with an average particle diameter between 2 and 30 micrometers, and
 i) 0 to 30% by weight of further pharmaceutically customary auxiliaries, where the constituents f) to i) add up to 100% by weight, and
D) is 0-15% by weight of further customary auxiliaries, where the components A) plus B) plus D) add up to 100% by weight, having a disintegration time of at most 45 seconds.

In one particularly preferred embodiment, the orally rapidly disintegrating, solid coated dosage form consists of a solid core consisting of component A), B) and D) coated with at least one film coating C), where
A) is a least 60% by weight of an auxiliary mixture in the form of agglomerates, where the agglomerates consist of
 a) 75 to 95% by weight of mannitol or erythritol or a mixture thereof,
 b) 3 to 15% by weight of crospovidone with an average particle size of from 5 to 30 micrometers and a hydration capacity of at least 7 g/g,
 c) 2 to 10% by weight of polyvinyl acetate,
 d) 0.01 to 2% by weight of at least one water-soluble polymer, and
 e) 0.001 to 2% by weight of further pharmaceutically customary auxiliaries, and the sum of the constituents a) to e) is 100% by weight,
B) is at least one active ingredient in amounts of up to 40% by weight, and D) is 0-15% by weight of further pharmaceutically customary auxiliaries,
where the components A), B) and D) add up to 100% by weight, and the film coating C) consists of
 f) 20 to 59.5% by weight of the rapidly water-soluble polyethylene glycol-vinyl acetate graft polymer of polyethylene glycol and vinyl acetate, where the polymerized vinyl acetate units have been completely or partially hydrolyzed,
 g) 40 to 70% by weight of at least one pigment,
 h) 0.5 to 10% by weight of a finely divided crospovidone with an average particle diameter between 2 and 15 micrometers, and
 i) 0 to 15% by weight of further, pharmaceutically customary auxiliaries,
where constituents f) to i) add up to 100% by weight, having a disintegration time of at most 45 seconds.

Furthermore, a rapidly disintegrating, solid coated dosage form in the form of a tablet has been found, where the tablet disintegrates in an aqueous medium, in particular in the aqueous medium of the mouth, within 60 seconds, preferably within 45 seconds, particularly preferably within 30 seconds and very particularly preferably within 20 seconds. The tablets also have, at 37° C. in phosphate buffer, pH 7.2, a disintegration time of less than 60 seconds, preferably less than 45 seconds and particularly preferably less than 30 seconds, the disintegration time being determined in the disintegration tester according to USP.

These are particularly preferably the disintegration times determined in the mouth.

The determination in the mouth is carried out here using a test group of at least ten people instructed or experienced in the testing of such dosage forms, the most uniform possible distribution of women and men being desired. The dry dosage form to be tested is placed onto the upper side of the tongue with a normal amount of saliva in the mouth and without consuming water or other liquids. The tablet is left to lie on the tongue without chewing or grinding movements of the tongue and teeth. By means of gentle pressure against the roof of the mouth, it is determined whether the tablet has completely disintegrated. The time until complete disintegration is determined. An average value from at least three individual determinations per test person is formed here per person. The average values from the individual test persons are in turn used to give an average for the dosage form to be tested. The result is the disintegration time in the mouth for this dosage form.

A method of producing rapidly disintegrating, solid coated dosage forms has likewise been found, wherein a solid core consisting of the components A), B) and D), where
A) is at least 60% by weight of an auxiliary mixture consisting of
 a) 60 to 97% by weight of at least one sugar or sugar alcohol,
 b) 1 to 25% by weight of disintegrant,
 c) 0 to 30% by weight of at least one film-forming polymer,
 d) 0 to 15% by weight of at least one water-soluble polymer,
 e) 0 to 15% by weight of further customary auxiliaries, where the constituents a) to e) add up to 100% by weight,
B) is up to 40% by weight of at least one active ingredient, and
D) is 0-15% by weight of further customary auxiliaries, where the components A) plus B) plus D) add up to 100% by weight, is coated with a film coating C) consisting of
- f) 20 to 70% by weight of a rapidly water-soluble polyether-vinyl ester graft polymer of polyether and vinyl ester, where the polymerized vinyl esters have been completely or partially hydrolyzed,
- g) 0 to 70% by weight of at least one pigment,
- h) 0 to 30% by weight of a finely divided crospovidone with an average particle diameter between 2 and 30 micrometers, and
- i) 0 to 30% by weight of further customary auxiliaries, where the constituents f) to i) add up to 100% by weight, where, at the start of the film coating application to the core, processing is carried out at an exit-air moisture content of at most 40%.

These cores are preferably orally rapidly disintegrating, solid coated dosage forms. The dosage forms preferably have the form of pellets or tablets, particularly preferably tablets. This dosage form have a disintegration time of at most 45 seconds.

In one preferred embodiment of the method, the film coating C) consists of
- f) 20 to 70% by weight of a rapidly water-soluble polyether-vinyl ester graft polymer of polyether and vinyl ester, where the polymerized vinyl esters have been completely or partially hydrolyzed,
- g) 0 to 70% by weight of at least one pigment,
- h) 0 to 30% by weight of a finely divided crospovidone with an average particle diameter between 2 and 30 micrometers, and
- i) 0 to 30% by weight of further, customary auxiliaries.

The dosage forms obtained or obtainable by this method are preferably orally rapidly disintegrating, solid coated dosage forms. The dosage forms obtained or obtainable by this method preferably have the form of pellets or tablets, particularly preferably tablets, very particularly preferably tablets with a diameter of from 1 to 10 mm. This dosage form have a disintegration time of at most 45 seconds.

In a further preferred embodiment of the method, to prepare the component A), sugars or sugar alcohol particles (constituent a)) and disintegrants (constituent b)) is firstly agglomerated with an aqueous solution or dispersion of the film-forming polymer (constituent c)) and dried and, only then, mixed with the other constituents d) and e).

In a further preferred embodiment of the method, the aqueous solution or dispersion of the film-forming polymer c) used for the agglomeration of the constituents a) and b) additionally comprises suspended, further disintegrant b).

In a further preferred embodiment of the method, to produce the agglomerates of the auxiliary mixture A), the components B) and D) are also used so that the agglomerates comprise the substances a), b), c), optionally d), optionally e), B) and optionally D). Each agglomerate particle thus comprises these components/constituents in the stated percentages by weight, the sum of a), b), c), d), B) and D) adding up to 100 percent by weight.

In a further preferred embodiment of the method, the auxiliaries e) and i), independently of one another, are one or more substances selected from the group consisting of acidifying agents, sweeteners, aromas, flavor enhancers, dyes, thickeners, surfactants and/or finely divided pigments.

All of these embodiments of the method can be combined with one another in twos or more.

Furthermore, the use of rapidly disintegrating, coated solid dosage forms for pharmaceutical applications, applications in the area of food, food supplement, animal nutrition, veterinary medicine and animal feed supplement has been found.

The rapidly disintegrating, solid coated dosage form according to the invention is particularly preferred for pediatric and geriatric applications and in controlling addiction, very particularly preferably for pediatric application.

Preferably, the dosage forms according to the invention are used as orally rapidly disintegrating pellets and tablets, very particularly preferably as tablets.

A particular advantage of the rapidly disintegrating, solid coated dosage form is that it can be colored by means of a colored coating. Similarly, a shiny surface is achieved which is not obtainable without a coating or has a considerably lower shine. It is a further advantage that as a result of the coating, it is possible to achieve protection for example against light, air and/or oxygen, meaning that, for example, the stability of the dosage form and in particular of the active ingredient are improved compared with a dosage form without film coating. Furthermore, particular flavor effects are possible in that the coating and the core can be aromatized independently of one another, for example with a flavor effect of the coating which differs from the flavor effect of the underlying core: thus, the coating can have a somewhat sweet flavor of, for example, strawberry, and the core can have a somewhat sour flavor of, for example, lemon. As a result, different flavor experiences can be achieved within a short sequence, e.g. sweet/sour or generally flavor 1/flavor 2. It is of course also possible for two or more coatings with different flavor effects to be applied to a core, likewise provided for example with a flavor effect.

It is likewise possible with this invention to incorporate active ingredients into the coating which are present in dissolved or dispersed form. Thus, for example, active ingredients that are incompatible with one another can be very readily incorporated into a rapidly disintegrating dosage form. The formulation of an active ingredient which is incompatible with the ingredients of the core, for example does not have long-term storability, is also possible. Separate granulation of an active ingredient can in each case be dispensed with. As a result, the possibility of relatively large active ingredient granules causing a sandy mouth feel also does not apply. Of suitability for the use of active ingredients in the coating are in particular those substances which are used in a low dose. Within the context of this invention, "low" dose means a dose between 0.01 and 10 mg per individually dosed form, as are usually used for highly active ingredients such as in particular for hormones.

The option of applying color for example for distinguishability, the option of applying flavor and/or different flavor experiences, the improved protection of the dosage form against external influences and/or better handleability, for example as a result of higher mechanical strength of the dosage form on account of the coating, is particularly advantageous.

The dosage form according to the invention can be configured in a particularly variable manner especially in the form of small tablets and pellets with diameters of in each case about 0.5 to 10 mm, preferably 1 to 5 mm, such that the dosage of the active ingredient content can be readily adapted to the person to be treated, in particular to their body weight. Thus, such small dosage forms can for example be readily counted or be measured using suitable dosage devices in order to achieve the desired dose. As a result of the protective coating, the dosage forms according to the invention are particularly well suited for this because the coating on the one hand protects the core and the active ingredient against external influences, and on the other hand, besides organoleptic and optical properties such as color and flavor, also improves the mechanical properties of the rapidly disintegrating, coated solid dosage form: the friction is lower, the greater the hardness, the better the permeability and the lower the sensitivity to moisture. Consequently, such dosage forms according to the invention are particularly suitable for use for children, for large packagings of the dosage forms such as screw-top containers, and also for regions with particularly extreme conditions such as high atmospheric humidity and/or temperature.

The administration forms to be coated can be in the form of tablets, pellets, capsules or extrudates. Within the context of the invention, these are referred to in each case as the "core".

To produce the core of the rapidly disintegrating, solid coated dosage form according to the invention, it is in principle possible to use any known technology and any known composition. Thus, for example, the cores of the rapidly disintegrating, solid coated dosage forms based on commercially supplied products and technologies such as Pharmaburst® and the compositions known from U.S. Pat. No. 7,118,765 B2, F-Melt® and the compositions disclosed in EP-A 1523974, AdvaTab®, the technology of RXCipient®, Orasolv®, Durasolv®, Zydis® etc., and also the other products and technologies known to the person skilled in the art can be used, which are known to the person skilled in the art in the field of rapidly disintegrating dosage forms, in particular orally rapidly disintegrating dosage forms (referred to as "orally dispersible tablets"/"orally disintegrating tablets" or for short "ODT").

To produce the core of the rapidly disintegrating, solid coated dosage form according to the invention, preference is given to using a preparation in the form of agglomerates. The preparation in the form of agglomerates comprises here preferably an auxiliary mixture consisting of a) 60-97% by weight of at least one sugar or sugar alcohol or mixtures thereof, b) 1-25% by weight of a disintegrant, c) 1-15% by weight of water-insoluble polymers, d) 0-15% by weight of water-soluble polymers, and e) 0-15% by weight of further, in particular pharmaceutically customary auxiliaries, where the sum of the constituents a) to e) is 100% by weight.

The preparations comprise, as constituent a), 60 to 97% by weight, preferably 70 to 95% by weight, particularly preferably 75 to 93% by weight, of a sugar, sugar alcohol or mixtures thereof. Suitable sugars or sugar alcohols are trehalose, mannitol, erythritol, isomaltol, maltitol, lactitol, xylitol, sorbitol. The sugars or sugar alcohols are preferably finely divided, with average particle sizes of from 5 to 100 μm (average particle size D[4,3]). If desired, the particle sizes can be adjusted by grinding. Preferred particle sizes are 30 to 50 μm. It may, however, also be advisable to use particle sizes less than 30 μm. It may likewise be recommended to use sugars or sugar alcohols which comprise mixtures of fractions with a different particle size, for example mixtures of 30 to 70% by weight of a grain size fraction with an average particle size of less than 30 μm and 30 to 70% by weight of a grain size fraction with an average particle size of from 30 to 50 μm. Preference is given to using mannitol, erythritol or mixtures thereof. The use of mannitol is particularly preferred.

As constituent b), disintegrants are used in amounts of from 1 to 25% by weight, preferably 2 to 15% by weight, particularly preferably 3 to 10% by weight. Such disintegrants are water-insoluble, but not film-forming. Disintegrant b) here is one or more substances selected from the group of substances also referred to as "superdisintegrants" and consisting of crospovidone, croscarmellose, crosslinked sodium or potassium carboxymethyl starch and L-hydroxypropylcellulose. Croscarmellose is a crosslinked carboxymethylcellulose, where, according to the invention, the sodium and calcium salts of croscarmellose are also intended as croscarmellose. Also of suitability are sodium and calcium carboxymethyl starch. Likewise of suitability is L-hydroxypropylcellulose, preferably with 5 to 16% hydroxypropoxy groups. Crospovidone is also suitable.

"Crospovidone" is a name, customary in the pharmaceutical sector, for water-insolubly crosslinked polyvinylpyrrolidone. Such substances are commercially available, for example, as Kollidon® CL, Kollidon® CL-F and Kollidon® CL-SF from BASF SE, Germany, and also as Polyplasdone® XL and Polyplasdone® XL-10 from International Speciality Products, USA. These substances are suitable as disintegrants and are also recommended as such by the manufacturers. Also suitable, furthermore, are the crospovidones Kollidon® CL-M from BASF and Polyplasdone® INF-10 from International Speciality Products, the very small particle sizes of which have been obtained by micronization, for which reason, they bring about substantially longer disintegration times than the products specified above in the case of identical use. The average particle sizes (the value D[4,3] is stated in micrometers, determined by means of laser defractometry using a Malvern Mastersizer X at a compressed-air atomization of 2 bar) and the hydration capacities of the specified products are given in the table.

TABLE

Particle sizes and hydration capacities of commercial crospovidones

| Product | Mean particle size D[4,3] in micrometers | Hydration capacity [g of water/g of polymer] |
|---|---|---|
| Kollidon CL | 118 | 4.4 |
| Kollidon CL-F | 29 | 5.9 |
| Kollidon CL-SF | 17 | 7.9 |
| Kollidon CL-M | 5 | 3.9 |
| Polyplasdone XL | 145 | 5.8 |
| Polyplasdone XL-10 | 27 | 4.6 |
| Polyplasdone INF-10 | 5 to 10 or 10* | <5 |

(*data from the manufacturer ISP, USA)

The disintegrant b) used is crospovidone with an average particle diameter between 2 and 150 micrometers. Preference is given to crospovidone with an average particle size of from 5 to 60 micrometers, particularly preferably from 10 to 35 micrometers, very particularly preferably 12 to 25 micrometers.

A crospovidone used as disintegrant b) particularly preferably has a hydration capacity of at least 7 g/g. The hydration capacity was determined as described above.

As constituent c), film-forming polymers are used in amounts of from 1 to 15% by weight, preferably 1 to 10% by weight. These are water-insoluble, film-forming polymers. Preference is given to polymers which are insoluble in the pH range from 1 to 14, i.e. have a pH-independent insolubility in water at any pH. Furthermore, polymers which are water-insoluble at any pH in the pH range from 6 to 14 are also suitable.

The polymers should be film-forming polymers. In this connection, film-forming means that the polymers in aqueous dispersion have a minimum film formation temperature of from −20 to +150° C., preferably 0 to 100° C.

Suitable water-insoluble, film-forming polymers are polyvinyl acetate, ethylcellulose, methyl methacrylate-ethyl acrylate copolymers, ethyl acrylate-methyl methacrylate-trimethylammonium ethyl methacrylate terpolymers. Butyl methacrylate-methylmethacrylate-dimethylaminoethyl methacrylate terpolymers.

The acrylate-methacrylate copolymers are described in more detail in the European Pharmacopeia as polyacrylate dispersion 30%, in the USP as Ammonio Methacrylate Copolymer and in JPE as Aminoalkyl-Methacrylate Copolymer E.

A preferred constituent c) used is polyvinyl acetate and/or ethylcellulose. Polyvinyl acetate can be used as aqueous dispersion with solids contents of from 10 to 45% by weight. Moreover, preference is given to polyvinyl acetate with a molecular weight between 100 000 and 1 000 000 daltons, particularly preferably between 200 000 and 800 000 daltons.

Particular preference is given to the use of a dispersion comprising polyvinyl acetate or a powder which has been obtained by drying such a dispersion.

In a further particularly preferred embodiment, ethylcellulose is used as constituent c). Mixtures of polyvinyl acetate and ethylcellulose are also possible.

Furthermore, the formulations can comprise, as constituent d), water-soluble polymers in amounts of from 0 to 15% by weight, preferably 0.01 to 10% by weight, particularly preferably 0.05 to 7% by weight and very particularly preferably 0.1 to 3% by weight. Suitable water-soluble polymers are, for example, polyvinylpyrrolidones, vinylpyrrolidone-vinyl acetate copolymers, polyvinyl alcohols, polyvinyl alcohol-polyethylene glycol graft copolymers, polyethylene glycols, ethylene glycol-propylene glycol block copolymers, hydroxypropylmethylcellulose, hydroxypropylcellulose, hydroxyethylcellulose, carrageenans, pectins, xanthans, alginates. Preferred water-soluble polymers are polyvinylpyrrolidones and vinylpyrrolidone-vinyl acetate copolymers. Particularly preferred water-soluble polymers are polyvinylpyrrolidones.

If desired, by adding customary, in particular pharmaceutically customary, auxiliaries (constituent e)) in amounts of from 0 to 15% by weight, for example such as acidifying agents, buffer substances, sweeteners, aromas, flavor enhancers and dyes, it is possible to further improve the flavor and appearance of the tablets obtained from the formulations. The following substances are particularly suitable here: citric acid, tartaric acid, ascorbic acid, sodium dihydrogenphosphate, cyclamate, saccharine-sodium, aspartame, natural, nature-identical and artificial flavorings such as menthol, peppermint aroma, fruit aromas and vanilla aroma, glutamate, riboflavin, betacarotene, water-soluble dyes, and finely divided colored lakes. By adding thickeners such as high molecular weight polysaccharides it is possible to additionally improve the mouth feel by increasing the softness and the volume feel. The amount of thickener in the core is usually selected here such that the disintegration of the core is not delayed, or not delayed to a noteworthy extent, as a result. If required, the effect of the thickener can be compensated for by increasing the amount of disintegrant. Furthermore, surfactants may also be added as constituent e). Suitable surfactants are, for example, sodium lauryl sulfate, dioctyl sulfosuccinate, alkoxylated sorbitan esters such as Polysorbat 80, polyalkoxylated derivatives of castor oil or hydrogenated castor oil, for example Cremophor® RH 40, alkoxylated fatty acids, alkoxylated hydroxy fatty acids, alkoxylated fatty alcohols, alkali metal salts of fatty acids and lecithins such as magnesium stearate.

Furthermore, to further improve the disintegration, finely divided pigments can also be added as constituent e) because they increase the internal interfaces, and water can therefore penetrate more rapidly into the tablet. These pigments, such as iron oxides, titanium dioxide, colloidal or precipitated silica, calcium carbonates, calcium phosphates, naturally have to be very finely divided, otherwise a grainy flavor will again arise.

Preferred constituents e) are surfactants such as, in particular, sodium lauryl sulfate and magnesium stearate.

The preparation of the pharmaceutical formulation in the form of agglomerates corresponding to component A) of the present invention is described in WO 2008/148733, (page 5, line 7 to page 6, line 25 and examples) and WO2007/071581 (page 5, line 25 to page 7, line 11 and examples) to the disclosure of which reference is hereby expressly made in its entirety.

In a further preferred embodiment, to produce the agglomerates A), a mixture of the constituents a) to e) and also additionally components B) and D) is used, where B) and D) are used separately or together as a mixture with the constituents a) and/or b) and otherwise the production methods disclosed in WO 2008/148733 and WO2007/071581 are followed.

Particular preference is given to a pharmaceutical formulation in the form of agglomerates, as is obtainable as Ludiflash® from BASF SE, Ludwigshafen. This is an auxiliary mixture in the form of agglomerates consisting of 90 percent by weight of mannitol, 5 percent by weight of Kollidon® CL-SF from BASF SE (a crospovidone with an average particle size of 17 micrometers and a hydration capacity of more than 7 g/g) and 5 percent by weight (based on the solids content) of Kollicoat® SR 30 D from BASF SE (a polyvinylacetate dispersion which comprises polyvinylpyrrolidone with K value 30 and sodium lauryl sulfate).

The mannitol used here has a particle size between 15 and 100 micrometers, preferably between 20 and 70 micrometers and particularly preferably between 20 and 50 micrometers, such as, for example, 25, 30, 35, 40 or 45 micrometers.

As regards the active ingredients B), there are no limitations for the dosage forms according to the invention. It is possible to use active ingredients from all indication areas, human drugs and animal drugs, vitamins, carotinoids, nutraceuticals, food supplements, mineral substances, micronutrients, substances from traditional medicine, natural substances and natural extracts etc. The active ingredients can have different physicochemical properties such as lipophilicity, solubility, grain size, grain structure, surface etc.

The dosage forms according to the invention are particularly suitable for producing medicaments of the active ingredient specified in each case in WO 2006/002808 and the dosages preferred therein, it also being possible to use the active ingredient in a taste-masked form, for example as coated, fine granules.

For the production of the cores of the solid coated dosage forms, the customary methods can be used, with direct tableting and roll compaction offering particular advantages. On account of the special properties of the auxiliary mixture used according to the invention in the form of agglomerates, as a rule only active ingredient, auxiliary mixture and a lubricant are required to produce the core. The formulation is very simple, very reproducible and the method can be easily validated. Such dosage forms are then provided with the film coating according to the invention by known methods. The lubricant may be present here in the mixture A) or be used as an external lubricant D). The use of external lubricants is sufficiently known to the person skilled in the art.

The principle of compaction is described in the book "Die Tablette", W. Ritschel and A. Bauer-Brandl, 2nd edition, 2002, Editio Cantor Verlag Aulendorf under the chapter Trockene Granulation [Dry Granulation]. Preference is given to using so-called roll compactors in which the starting material is compressed between 2 rotating rolls and is then comminuted again to give coarser granule particles. The comminution here should take place as gently as possible so that few fines are produced. The pressing forces to be applied are between 0.5 and 20 kN/cm, preferably between 1 and 10 kN/cm. It has proven to be advantageous to use the lowest possible pressing forces which just lead to a stable compact because then the breaking strength of the tablets produced therefrom is at its highest. Preferably, the comminution takes place by means of a sieve granulator with mesh widths of from 0.5 to 3 mm.

The resulting compacts generally have an average particle size between 0.2 and 2 mm, preferably between 0.3 and 1 mm.

The compacts can be processed in the usual manner to give tablets. In this regard, the admixing of further lubricant (constituent e) is usually helpful. In one particularly preferred embodiment, additional disintegrant b) is also mixed in at this stage. Tableting takes place on customary rotary presses, it being possible to produce both biplanar or curved shapes as well as oblong or football shaped shapes.

The roll compaction of a mixture corresponding to component A) of the present invention is shown in the examples in WO2008/148731, to which reference is hereby expressly made.

The methods of tableting and producing pellets is sufficiently known to the person skilled in the art.

Coating several times with the same or different film coating C) is likewise possible and encompassed by the present invention: thus, a formulation in the form of agglomerates of A), of A) and D), of A) and B) or of A), B) and D) can be coated with film coating C) and then compressed to give the solid dosage form. This dosage form can then be coated with a further film coating C).

Film coatings C) for the inventive rapidly disintegrating, solid coated dosage forms which are used are rapidly water-soluble, film-forming polymers. In principle, all water-soluble film formers are suitable as coating compositions.

As regards the solubility of the polymers, the terms "water-soluble" and "sparingly water-soluble" are to be understood as follows: the term "water-soluble" means that for a solution of the polymer in water at 20° C., 1 to 30 g of water are required per g of polymer. According to the invention, the term "sparingly water-soluble" includes poorly soluble, sparingly soluble and also virtually insoluble substances and means that for a solution of the polymer in water at 20° C., from 30 g to 1000 g of water are required per g of polymer. In the case of virtually insoluble substances, at least 10 000 g of water are required per g of substance. The substances referred to according to the invention as water-soluble polymers are water-soluble over the entire pH range.

In the description below, the term "sparingly soluble" is shorthand for "sparingly soluble in water".

Among the sparingly soluble polymers are also listed those polymers which are not soluble over the full pH range, but exhibit a pH-dependent solubility. Suitable film coatings are known, for example, from WO 2006/002808. The film coatings disclosed therein exhibit, in powder form, no separation of any kind between the individual constituents, such as in particular not between pigments and polymers, are flowable to an excellent degree, very easy and quick to dissolve and/or to disperse in water, thus giving rise to a very short production time for the spray preparation, can be sprayed in high polymer and solids concentrations, can be sprayed at a high spraying rate, without the spray nozzle becoming blocked, spread very readily on the surface, are flexible, do not have any kind of cracking during storage, are not sticky and nevertheless adhere well to all surfaces, exhibit excellent smoothness and shine and/or are very stable towards mechanical stress. Nevertheless, they exhibit a very rapid dissolution in water as in the mouth.

The film-forming polymers f) used are preferably rapidly water-soluble polyether-vinyl ester graft polymers of polyalkylene glycol and vinyl ester, where the polymerized vinyl esters have been completely or partially hydrolyzed.

Particular preference is given to using rapidly water-soluble polyethylene glycol-vinyl acetate graft polymers with vinyl acetate units completely or partially hydrolyzed after the polymerization.

Very particular preference is given to rapidly water-soluble polyethylene glycol-vinyl acetate graft polymers with vinyl acetate units hydrolyzed after the polymerization and having a degree of hydrolysis of from 90 to 99 mol percent (based on the vinyl acetate units).

Preferred film-forming polymers as constituent f) in the film coating C) are the polyvinyl alcohol-polyether graft copolymers known from WO 2006/002808. Preferred film coatings C) are the film coatings known from WO 2006/002808 comprising these polyvinyl alcohol-polyether graft copolymers. Reference is therefore made here to the corresponding disclosures of the polyvinyl alcohol-polyether graft copolymers as film-forming polymers on page 3, line 17 to page 5, line 18 and the film coatings obtainable therefrom in WO 2006/002808 in their entirety. Particular preference is given to pulverulent film coatings C), consisting of f) 20 to 70% by weight, preferably 25 to 65% by weight and particularly preferably 30 to 60% by weight, of a polyvinyl acetate-polyalkylene ether graft copolymer completely or partially hydrolyzed after the polymerization, g) 0 to 70% by weight, preferably 10 to 70% by weight, particularly preferably 40 to 70% by weight and very particularly preferably 60 to 70% by weight of one or more organic or inorganic pigments with an average particle size of less than 8 micrometers, preferably less than 6 micrometers and particularly preferably less than 4 micrometers, where the particle size of the pigment has been determined on the pigment particles embedded in the polymers of the solid film coating, h) 0 to 30% by weight, preferably 0.5 to 15% by weight and particularly preferably 1 to 5% by weight, of a crospovidone with an average particle diameter between 2 and 30 micrometers, preferably with a hydration capacity of more than 7 g/g, and i) 0 to 30% by weight, preferably 0.5 to 20% by weight and particularly preferably 1 to 10% by weight, of further customary, preferably pharmaceutically customary auxiliaries in film coating compositions. The sum of the constituents f) to i) adds up here to 100% by weight.

A particularly preferred constituent f) is Kollicoat® IR, a polyvinyl alcohol-polyether graft copolymer from BASF SE, Ludwigshafen, which corresponds to the monograph "Macrogol Poly(vinyl alcohol) Grafted Copolymer" in European Pharmacopeia 6.7. This is a polyvinyl acetate-polyethylene glycol graft copolymer with vinyl acetate units hydrolyzed after the polymerization and having a degree of hydrolysis of from 90 to 99 mol percent, stated in the European Pharmacopeia as "Polymer with 75% polyvinyl alcohol and 25% polyethylene glycol in powder form". The viscosity as 20% strength aqueous solution is between 50 and 250 mPas. The molecular weight is between 30 000 and 150 000 daltons, the average molecular weight is preferably 45 000 g/mol.

Preference is likewise given to colored coatings based on a polyvinyl alcohol-polyether graft copolymer, in particular based on Kollicoat® IR, for example Kollicoat® IR White and Kollicoat® IR Coating Systems and individual colored coatings thereof, Kollicoat® IR Brillant Blue, Kollicoat® IR Carmine, Kollicoat® IR Sunset Yellow, Kollicoat® IR Red, Kollicoat® IR Yellow, Kollicoat® IR Black and Kollicoat® IR White II, where "colored" coating also includes "white" coatings (which thus comprise only "white pigments" such as titanium dioxide).

WO 2006/002808 describes constituent g) in the film coating (WO 2006/002808, page 5, line 25 to page 6, line 2), the preparation of the film coating compositions (WO 2006/002808, page 6, line 25 to page 8, line 12) and their use and method for coating solid dosage forms (WO 2006/002808, page 8, lines 34 to 42, page 10, lines 29 to 36 and examples) in detail, to which reference is likewise expressly made here.

It has likewise been found that a high concentration of pigment g) in the coating offers advantages with regard to a particularly short dissolution time of the coating and thus the disintegration time of the core, such as, in particular, of a tablet. The pigment concentration in the coating is therefore in accordance with the invention—if pigments are used—at least 40% by weight, preferably at least 50% by weight and particularly preferably at least 60% by weight. The pigment particles are particularly preferably present in micronized form with an average particle size of less than 8 micrometers, preferably less than 6 micrometers and particularly preferably less than 4 micrometers, where the particle size of the pigment particles has been determined on the pigment particles embedded in the polymers of the solid film coating composition. For this, the pigment particles are preferably comminuted to the desired particle sizes in the presence of the other constituents f) and i) in aqueous suspension. Such a procedure is described in WO 2006/002808 (page 6, line 25 to page 8, line 12), to which reference is likewise expressly made.

It has likewise been found that further constituents in the film coating can have a positive influence on the rapid dissolution of the coating:
water-swelling, water-insoluble substances, such as the so-called "superdisintegrants", such as in particular crospovidone or celluloses, such as preferably microcrystalline cellulose (MCC) can be used as constituent h). As constituent h), preference is given to using crospovidone, in particular those with very small particle sizes of not more than 30 micrometers, preferably not more than 20 micrometers and particularly preferably not more than 10 micrometers and very particularly preferably not more than 8 micrometers average particle size.

As constituent h), very particular preference is given for example to Kollidon CL-M, a crospovidone with an average particle size of about 5 micrometers.

By using these finely divided crospovidones, several advantages have been achieved in one step: a very pleasant, "soft" mouth feel upon dissolution has been observed and a rough, sandy feel avoided. By using particularly finely divided crospovidones below 10 micrometers such as Kollidon CL-M, it was possible to provide coated dosage forms according to the invention which have particularly thin film coatings. These thin film coatings can vary in the range from 5 to about 20 micrometers, preferably 8 to 15 micrometers without the crospovidones bringing about a roughness of the tablet surface. As a result, it was possible firstly to use little film coating composition in terms of weight, which brings cost advantages. Secondly, the small thickness of the film coating also minimizes the dissolution rate.

Within the context of this invention, "rapidly water-soluble film coating compositions" and "rapidly water-soluble film coatings" accordingly also means those film coatings and film coating compositions which, besides the rapidly water-soluble polymers, can also comprise water-insoluble substances such as crospovidones and pigments.

Consequently, according to the present invention, rapidly disintegrating, solid coated dosage forms, in particular tablets, with thin, rapidly water-soluble film coatings can be obtained, where the film coatings comprise water-insoluble, swelling substances, preferably finely divided crospovidones, in particular crospovidones with particle sizes up to 30 micrometers, preferably up to 20 micrometers and very especially preferably up to 10 micrometers, and also at least 40 percent by weight, preferably at least 50% by weight and particularly preferably at least 60 percent by weight of pigment with an average particle size of less than 8 micrometers, preferably less than 6 micrometers and particularly preferably less than 4 micrometers, the particle size of the pigment particles being determined on the pigment particles embedded in the polymers of the solid film coating composition.

As further customary, in particular pharmaceutically customary, auxiliaries i) in the film coating composition, taste and appearance of the tablets obtained from the formulations can be further improved for example with acidifying agents, buffer substances, sweeteners, aromas, flavor enhancers and dyes. The following substances are particularly suitable here: citric acid, tartaric acid, ascorbic acid, sodium dihydrogenphosphate, cyclamate, saccharin-sodium, aspartame, natural, nature-identical and artificial flavorings such as menthol, peppermint aroma, fruit aromas and vanilla aroma, glutamate, riboflavin, betacarotene, water-soluble dyes, and finely divided colored lakes.

Furthermore, surfactants may also be added as constituent i). Suitable surfactants are, for example, sodium lauryl sulfate, dioctyl sulfosuccinate, alkoxylated sorbitan esters, such as Polysorbate 80, polyalkoxylated derivatives of castor oil or hydrogenated castor oil, for example Cremophor® RH 40, alkoxylated fatty acids, alkoxylated hydroxyl fatty acids, alkoxylated fatty alcohols, alkali metal salts of fatty acids and lecithins, such as magnesium stearate. Preference is given to sodium lauryl sulfate and magnesium stearate.

A further film coating can also be applied to the core already coated with a first film coating, it being possible for this further film coating to differ in its composition from the first film coating. If two or more film coatings are used, then at least one film coating corresponds to the film coating C) according to the invention. Preferably, all film coatings correspond to the film coating C) according to the invention, although the two or more film coatings C) can differ from one another.

Thus, for example, firstly a colorless film coating 1 can be applied and then a gloss layer, firstly a colored film coating 1 and then a colorless film coating 2 or firstly a colored film coating 1 and then a colorless film coating 2.

The core can accordingly also carry as first film coating an intermediate layer film coating (referred to as "subcoating") which is not a film coating C). Such an intermediate layer is generally applied in order to specifically protect the active ingredient e.g. against water, oxygen, protons or chemical substances of the coating and also of the contents of the stomach and intestine.

A preferred second and any further film coating composition is likewise a film coating C). Preferably, a rapidly disintegrating, solid coated dosage form according to the invention, however, has only two film coatings, of which at least one is a film coating C). Particularly preferably, a rapidly disintegrating, solid coated dosage form according to the invention has only one film coating C).

Usually, the cores have a diameter of from 0.5 to 16 mm, preferably from 1.5 to 12 mm, particularly preferably from 2 to 10 mm. Cores in the form of pellets preferably have an oval to roundish shape. Dosage forms in the form of tablets preferably have a curved form. However, any other tablet form known to the person skilled in the art is also possible. The tensile strength of tablets, calculated according to the equation $$\sigma = 2F/\pi Dh,$$

where F is the breaking strength, D is the diameter and h is the tablet height, is at least 0.8 MPa (MPa=mega-Pascal), preferably at least 1 MPa and particularly preferably at least 1.2 MPa.

The rapidly disintegrating, solid coated dosage form is particularly preferably in the form of a tablet which has a curved shape, a diameter of from 1 to 16 mm, preferably of from 1.5 to 12 mm, especially preferably 2 to 10 mm, and a disintegration time in the mouth of less than 60 seconds, preferably less than 30 seconds and particularly preferably of less than 15 seconds, and the coating of which has a thickness of from 0.5 to 20 micrometers, preferably 1 to 15 micrometers and particularly preferably from 2 to 12 micrometers.

The coated solid dosage form according to the invention can advantageously also be used in the form of tablets which are left to disintegrate in a glass of water prior to use.

Various methods for coating solid dosage forms are described in detail for example in WO 2006/002808. All of these methods are suitable for the coating according to the invention of the rapidly disintegrating, coated solid dosage forms such as, in particular, tablets, for which reason reference is expressly made here to these methods. Of course, all other methods known to the person skilled in the art for applying film coatings are in principle also suitable. The method according to the invention for coating the rapidly disintegrating, solid coated dosage form has, in contrast to the methods known hitherto, initially a low relative exit-air moisture content which is adjusted to values of at most 40%, preferably at most 30%. Following application of 10 to 20% of the total amount of film coating composition preparation, the exit-air moisture content can be increased to values above 40%.

The total amount of film coating composition C) is 1 to 5 mg/cm$^2$, preferably 1.5 to 3 mg/cm$^2$, in each case based on the surface of the core to be coated.

Particularly suitable devices for applying the film coating are horizontal drum coaters and coaters in which the cores such as, in particular, tablets, are fluidized through a stream of air. However, it is also possible to use all other types known to the person skilled in the art, such as e.g. pan coaters or immersion blade coaters.

EXAMPLES

Preparation of the Cores: Tablets

The agglomerates were prepared in a fluidized bed (GPCG 3.1, Glatt) by means of top-spray methods: sugar alcohol and disintegrant (croscarmellose, crosslinked sodium carboxymethyl starch, L-hydroxypropylcellulose) were introduced as initial charge and agglomerated with aqueous binder dispersion. The aqueous binder dispersion used was a commercially available polyvinyl acetate dispersion (Kollicoat® SR30 D, BASF SE, 30 percent by weight in water). The L-hydroxypropylcellulose used was a type with a hydroxypropoxy content of 11%. On account of its coarse particulate nature, erythritol was firstly comminuted to give a fine powder (average particle size less than 50 μm).

TABLE 1

Formulation composition of agglomerates A to D in % by wt.

| | A | B | C | D |
|---|---|---|---|---|
| Lactose (Granulac ® 230) | 93 | — | — | — |
| Mannitol (Pearlitol ® 50 C) | — | 90 | — | — |
| Mannitol (Pearlitol ® 25 C) | — | — | 90 | 45 |
| Erythritol (Eridex ® 16952) | — | — | — | 45 |
| crosslinked PVP (Kollidon CL-SF) | 3.5 | 5.0 | 5.0 | 5.0 |
| Kollicoat SR 30 D (data based on solids content) | 3.5 | 5.0 | 5.0 | 5.0 |

TABLE 2

Formulation compositions E to J in % by wt.

| | E | F | G | H | J |
|---|---|---|---|---|---|
| Mannitol (d$_{0.5}$: 36 μm] | 90 | 90 | 90 | 44 | 76 |
| Erythritol (d$_{0.5}$: 44 μm] | — | — | — | 44 | — |
| Sorbitol (d$_{0.5}$: 47 μm] | — | — | — | — | 11 |
| Croscarmellose-sodium | 5 | — | — | — | 4 |
| Croscarmellose-calcium | — | — | — | 8 | — |
| crosslinked sodium carboxymethyl starch | — | 5 | — | — | 3 |
| L-Hydroxypropylcellulose | — | — | 5 | — | — |
| Kollicoat SR 30 D (data based on solids content) | 5 | 5 | 5 | 4 | 6 |

In a two-stage agglomeration process in which firstly a lower spraying rate has been selected and then the spraying rate has been increased, the following preparation parameters were used (spray conditions):

| | |
|---|---|
| Batch size: | 0.6 kg |
| Concentration of the binder solution-dispersion: | 10% by weight |
| Inlet air temperature: | 55° C. |
| Exit air temperature in the first 10 minutes: | 35° C. |
| Exit air temperature from the 11th minute: | 25° C. |
| Spraying rate in the first 10 minutes: | 7.5 g/min |
| Spraying rate from the 11th minute: | 20 g/min |

TABLE 3

Preparation conditions for formulations E to J

| | E | F | G | H | J |
|---|---|---|---|---|---|
| Inlet air temperature [° C.] | 49 | 52 | 52 | 51 | 53 |
| Exit air temperature [° C.] | 25 | 28 | 31 | 27 | 31 |

Spraying rate for experiments D to H: 15 g/min for the first 10 minutes, then 20 g/min The agglomerates A to D prepared in this way were mixed with 0.5 to 1.0% by weight, the agglomerates E to J with 2% by weight of lubricant (magnesium stearate) in a Turbula mixer for 5 min. These mixtures were then tableted on a fully instrumented tableting press (A to C: rotary tableting press Korsch PH 100/6; rotational speed of 30 rpm, 6 punches with 10 mm, biplanar, facetted); (D to H: fully instrumented eccentric press Korsch XP1, at 30 strokes/min, punch with 10 mm, biplanar, facetted). The tablet weight was adjusted to 300 mg. In the case of A to C, a tableting was firstly carried out at a pressing force of 18 kN (the tablets had different degrees of hardness depending on the compressibility of the powder), then in the case of A to C, the pressing force was adjusted in each case such that the breaking strength of the tablets was 60 N. In the case of D to H, the pressing force was adjusted such that tablets with a breaking strength of 40-60 N resulted.

The tablets were investigated with regard to breaking strength (tablet tester HT-TMB-CI-12 F, Kraemer), friability (Roche friabilator, Erweka) and disintegration time in phosphate buffer pH 7.2 (disintegration tester ZT 74, Erweka) and release rate in gastric juice (release device, Erweka). For numerical data with a slash, the data on the right-hand side of the slash is based on the tablets obtained using a pressing force of 18 kN, and the data on the left-hand side of the slash is based on tablets obtained using a pressing force of 60 kN.

TABLE 4

Tablet properties for formulations A to D

|   | Breaking strength [N] | Friability [%] | Disintegration time [s] |
|---|---|---|---|
| A | 180/60 | 0.05/0.15 | 45/<20 |
| B | 200/60 | 0.03/0.15 | 55/<20 |
| C | 200/60 | 0.02/0.15 | 57/<20 |
| D | 200/60 | 0.10/0.25 | 59/30 |

TABLE 5

Tablet properties

| | Tableting data | Tablet parameters | |
|---|---|---|---|
| | Pressing force [kN] | Breaking strength [N] | Disintegration time [s] |
| E | 4.0 | 49 | 15 |
| F | 3.7 | 51 | 21 |
| G | 3.8 | 40 | 53 |
| H | 5.3 | 52 | 38 |
| J | 4.6 | 51 | 32 |

Example 1

Preparation of a Tablet Core Containing Caffeine

| Composition: | |
|---|---|
| formulation B: | 201.25 mg |
| caffeine | 25 mg |
| Kollidon CL-SF | 18.75 mg |
| sodium stearyl fumarate | 5 mg |

The weighed-out auxiliaries and active ingredients were placed over a sieve with a mesh width of 1000 micrometers and mixed for 10 minutes using a Turbula T10B tumble mixer at 14 rpm. The ready-to-press mixture was compressed on a Korsch XL100 rotary press to give tablets with a weight of 250 mg, a breaking strength of 100 N and, resulting therefrom, a disintegration time of 18 seconds. The tablets had a diameter of 9 mm and a curved shape.

Example 2

Caffeine Film Tablet

The tablet from example 1 was further processed in an Innojet coater to give a rapidly disintegrating film tablet at an inlet-air temperature of 50° C. and a product temperature of 35° C. under otherwise identical spraying conditions.

Spraying medium: 20% strength by weight aqueous Kollicoat IR solution; disintegration times of the coated tablets: 25 seconds for an application amount of 2 mg/cm$^2$ and 38 seconds for an application amount of 3 mg/cm$^2$.

Example 3

Caffeine Film Tablet

Procedure analogous to example 2; spraying medium: 20% strength by weight of aqueous suspension (83.35% by weight of Kollicoat IR, 16.65% by weight of Kollidon CL-M); disintegration times of the coated tablets: 22 seconds for an application amount of 2 mg/cm$^2$, and 35 seconds for an application amount of 3 mg/cm$^2$.

Example 4

Caffeine Film Tablet

Procedure analogous to example 2; spraying medium: 20% strength by weight aqueous suspension (30% by weight Kollicoat IR, 35% by weight talc, 23.35% by weight titanium dioxide, 11.65% by weight Sicovit red); disintegration times of the coated tablets: 18 seconds for an application amount of 2 mg/cm$^2$ or 21 seconds for an application amount of 3 mg/cm$^2$ or 30 seconds for an application amount of 4 mg/cm$^2$.

Example 5

Preparation of a Tablet Core Containing Loperamide 2 mg

| Composition: | |
|---|---|
| formulation C | 96 mg |
| loperamide | 2 mg |
| Kollidon CL-SF | 1 mg |
| sodium stearyl fumarate | 1 mg |

Procedure analogous to example 1, weight: 100 mg, diameter 7 mm, curved shape, breaking strength: 50 N, disintegration time: 17 seconds Example 6

Loperamide Film Tablet with 1% by Weight Aspartame in the Film

Procedure analogous to example 2, but tablet from example 5; spraying medium: 20% strength by weight aqueous suspension (29% by weight of Kollicoat IR and 30% by weight of talc, 20% by weight of titanium dioxide, 10% by weight of Sicovit red, 1% by weight of aspartame); disintegration times of the coated tablets: 19 seconds in the case of an application amount of 2 mg/cm$^2$ or 24 seconds in the case of an application amount of 3 mg/cm² or 35 seconds in the case of an application amount of 4 mg/cm².

Example 7

Preparation of a Tablet Core Containing Loratadine 10 mg

| | Composition: | |
|---|---|---|
| I | formulation D | 39.75 mg |
| | loratadine | 10 mg |
| | saccharin-sodium | 0.25 mg |
| II | Kollidon 25 | 1 mg |
| III | formulation B | 145 mg |
| | magnesium stearate | 4 mg |

The weighed-out auxiliaries and active ingredients from I were granulated with an 8.5% strength by weight aqueous solution of II in a Glatt GPC G3 fluidized-bed granulator (atomization pressure 0.5 bar, inlet air temperature 45-50° C., exit air temperature 30° C.). The resulting granule grains were mixed with III for 10 minutes in a Turbula T10B tumble mixer and then placed over a sieve with a mesh width of 0.8 millimeters. The resulting ready-to-press mixture was compressed on a Korsch XL100 rotary press at a pressing force of 2.8 kN to give curved tablets with a weight of 200 mg, 8 mm diameter and, resulting therefrom, a disintegration time of 19 seconds.

Example 8

Loratadine Film Tablet with Grapefruit Aroma in the Film

Procedure analogous to example 2, but tablet from example 7; spraying medium: aqueous spray suspension (44% by weight of Kollicoat IR, 1% by weight of grapefruit aroma, 15% by weight of Kollidon CL-M, 20% by weight of talc, 13.5% by weight of titanium dioxide, 6.5% by weight of Sicovit red); disintegration times of the coated tablets: 18 seconds in the case of an application amount of 2 mg/cm² or 23 seconds in the case of an application amount of 3 mg/cm² or 33 seconds in the case of an application amount of 4 mg/cm².

Example 9

Preparation of a Minitablet (Diameter 2 mm) with 0.5 mg of Cetirizine×2HCl

| Composition: | |
|---|---|
| formulation B | 5.49 mg |
| cetirizine | 0.5 mg |
| Aerosil 200 | 0.07 mg |
| Avicel PH 101 | 0.7 mg |
| aspartame | 0.14 mg |
| Pruv | 0.1 mg |

Procedure analogous to example 1, weight: 7 mg, diameter 2 mm, curved shape, disintegration time: 6 seconds

Example 10

Cetirizine Minifilm Tablet

Procedure analogous to example 2, but tablet from example 9; spraying medium: aqueous spray suspension (40% by weight of Kollicoat IR, 10% by weight of Kollidon CL-M, 25% by weight of talc, 16.5% by weight of titanium dioxide, 8.5% by weight of Sicovit red); disintegration times of the coated tablets: 14 seconds in the case of an application amount of 2 mg/cm² or 17 seconds in the case of an application amount of 3 mg/cm² or 19 seconds in the case of an application amount of 4 mg/cm².

Example 11

Preparation of a Tablet Core Containing Acetaminophen

| Composition: | |
|---|---|
| F-Melt ® type C (Fuji Chemical Industry) | 118 mg |
| acetaminophen | 80 mg |
| magnesium stearate | 2 mg |

Procedure analogous to example 1, weight: 200 mg, diameter 8 mm, curved shape, breaking strength: 60 N, disintegration time: 25 seconds F-Melt type C is a mixture comprising synthetic dibasic calcium phosphate (Fujicalin®), mannitol, xylitol, inorganic substances and disintegrant.

Example 12

Acetaminophen Film Tablet

Procedure analogous to example 2, but tablet from example 11; spraying medium: 20% by weight of aqueous solution of Kollicoat IR; disintegration times of the coated tablets: 32 seconds in the case of 2 mg/cm² or 43 seconds in the case of 3 mg/cm²

Example 13

Preparation of a Tablet Core Containing Ascorbic Acid

| Composition: | |
|---|---|
| F-Melt ® type C (Fuji Chemical Industry) | 128.2 mg |
| ascorbic acid | 60 mg |
| Kollidon CL-SF | 10 mg |
| talc | 1 mg |
| magnesium stearate | 0.8 mg |

Procedure analogous to example 1, weight: 200 mg, diameter 8 mm, curved shape, breaking strength: 50 N, disintegration time: 19 seconds

Example 14

Ascorbic Acid Film Tablet

Procedure analogous to example 2, but tablet from example 13; spraying medium: 20% by weight of aqueous suspension (35% by weight of Kollicoat IR and 30% by weight of talc, 23.5% by weight of titanium dioxide and 11.5% by weight of Sicovit red); disintegration times of the coated tablets: 26 seconds in the case of 2 mg/cm$^2$ or 33 seconds in the case of 3 mg/cm$^2$ or 40 seconds in the case of 4 mg/cm$^2$.

Example 15

Preparation of Placebo Tablet Core

| Composition: | |
| --- | --- |
| Pharmaburst ® (SPI Pharma) | 294 mg |
| sodium stearyl fumarate | 6 mg |

Procedure analogous to example 1, weight: 300 mg, diameter 9 mm, curved shape, breaking strength: 65 N, disintegration time: 29 seconds Pharmaburst is a composition comprising disintegrant and a co-processed mixture of mannitol and sorbitol.

Example 16

Placebo Film Tablet

Procedure analogous to example 2, but tablet from example 15; spraying medium: 20% by weight of aqueous suspension (85% by weight of Kollicoat IR, 15% by weight of Kollidon CL-M); disintegration times of the coated tablets: 35 seconds in the case of 2 mg/cm$^2$ or 42 seconds in the case of 3 mg/cm$^2$ or 50 seconds in the case of 4 mg/cm$^2$.

The invention claimed is:

1. A rapidly disintegrating, solid coated dosage form comprising a solid core consisting of the components A), B) and D), wherein the solid core is coated with at least one film coating C), where
    A) is at least 60% by weight of an auxiliary mixture consisting of
        a) 60 to 97% by weight of at least one sugar or sugar alcohol,
        b) 1 to 25% by weight of disintegrant,
        c) 0 to 30% by weight of at least one film-forming polymer,
        d) 0 to 15% by weight of at least one water-soluble polymer,
        e) 0 to 15% by weight of further, customary auxiliaries,
    where the constituents a) to e) add up to 100% by weight,
    B) is up to 40% by weight of at least one active ingredient,
    C) is a film coating consisting of
        f) 20 to 70% by weight of a rapidly water-soluble polyether-vinyl ester graft polymer of polyether and vinyl ester, where the polymerized vinyl esters have been completely or partially hydrolyzed,
        g) 0 to 70% by weight of at least one pigment,
        h) 0 to 30% by weight of a finely divided crospovidone with an average particle diameter between 2 and 30 micrometers, and
        i) 0 to 30% by weight of further customary auxiliaries,
    where the constituents f) to i) add up to 100% by weight, and
    D) is 0-15% by weight of further customary auxiliaries, where the components A) plus B) plus D) add up to 100% by weight, and
    wherein the rapidly disintegrating, solid coated dosage form has a disintegration time of at most 45 seconds.

2. The dosage form according to claim 1, where the film-forming constituent f) is a rapidly water-soluble polyethylene glycol-vinyl acetate graft polymer, where the polymerized vinyl acetate has been hydrolyzed to more than 90% and the combined fraction of polyvinyl alcohol and polyvinyl acetate is 70 to 80% by weight and the fraction of polyethylene glycol is 20 to 30% by weight.

3. The dosage form according to claim 1, where the disintegrant b) is selected from the group consisting of crospovidone, croscarmellose, sodium or calcium carboxymethyl starch and L-hydroxypropylcellulose.

4. The dosage form according to claim 3, where the disintegrant b) is a crospovidone with an average particle size of from 2 to 30 micrometers.

5. The dosage form according to claim 1, where the fraction of pigment g) in the solid film coating C) is at least 40% by weight.

6. The dosage form according to claim 1, where
    b) is 1-25% by weight of at least one disintegrant selected from the group consisting of crospovidone, croscarmellose, sodium or calcium carboxymethyl starch and L-hydroxypropylcellulose, and
    c) is 1-15% by weight of at least one water-insoluble, film-forming polymer.

7. The dosage form according to claim 1, where
    a) is 75 to 95% by weight of mannitol or erythritol or a mixture thereof,
    b) is 3 to 15% by weight of crospovidone with an average particle size of from 5 to 30 micrometers and a hydration capacity of at least 7 g/g,
    c) is 2 to 10% by weight of polyvinyl acetate,
    d) is 0.01 to 2% by weight of at least one water-soluble polymer, and
    e) is 0.001 to 2% by weight of further pharmaceutically customary auxiliaries,
    and the sum of components a) to e) is 100% by weight.

8. A method of producing a rapidly disintegrating, solid coated dosage form comprising
    preparing a solid core consisting of the components A), B) and D), where
    A) is at least 60% by weight of an auxiliary mixture consisting of
        a) 60 to 97% by weight of at least one sugar or sugar alcohol,
        b) 1 to 25% by weight of disintegrant,
        c) 0 to 30% by weight of at least one film-forming polymer,
        d) 0 to 15% by weight of at least one water-soluble polymer,
        e) 0 to 15% by weight of further, customary auxiliaries,
    where the constituents a) to e) add up to 100% by weight,
    B) is up to 40% by weight of at least one active ingredient, and
    D) is 0-15% by weight of further customary auxiliaries,
    where the components A) plus B) plus D) add up to 100% by weight, and
    coating the solid core with a film coating C) consisting of
        f) 20 to 70% by weight of a rapidly water-soluble polyether-vinyl ester graft polymer of polyether and vinyl ester, where the polymerized vinyl esters have been completely or partially hydrolyzed,
        g) 0 to 70% by weight of at least one pigment,
        h) 0 to 30% by weight of a finely divided crospovidone with an average particle diameter between 2 and 30 micrometers, and i) 0 to 30% by weight of further customary auxiliaries,
where the constituents f) to i) add up to 100% by weight,
where, at the start of the film coating application to the core, processing is carried out at an exit-air moisture content of at most 40%.

9. The method according to claim 8, where, for producing component A), sugars or sugar alcohol particles (constituent a)) and disintegrant (constituent b)) are firstly agglomerated with an aqueous solution or dispersion of the film-forming polymer (constituent c)) and dried, and only then mixed with the other constituents d) and e).

10. The method according to claim 8, where the aqueous solution or aqueous dispersion of the film-forming polymer c) used for the agglomeration of constituents a) and b) comprises further disintegrant (constituent b)) in suspended form.

11. The method according to claim 8, where the agglomerates of the auxiliary mixture A) further comprise components B) and D) as constituents of the agglomerates.

12. The method according to claim 8, where the solid core is a tablet with a diameter of from 1 to 10 mm.

13. The method according to claim 8, where the auxiliaries e) and i), independently of one another, are selected from the group consisting of acidifying agents, sweeteners, aromas, taste enhancers, dyes, thickeners, surfactants and finely divided pigments.

14. The dosage form according to claim 1, wherein the film coating C) consists of
   f) 20 to 70% by weight of a rapidly water-soluble polyether-vinyl ester graft polymer of polyether and vinyl ester, where the polymerized vinyl esters have been completely or partially hydrolyzed,
   g) 10 to 70% by weight of at least one pigment,
   h) 0 to 30% by weight of a finely divided crospovidone with an average particle diameter between 2 and 30 micrometers, and
   i) 0 to 30% by weight of further customary auxiliaries,
where the constituents f) to i) add up to 100% by weight.

15. The dosage form according to claim 1, wherein the film coating C) consists of
   f) 20 to 70% by weight of a rapidly water-soluble polyether-vinyl ester graft polymer of polyether and vinyl ester, where the polymerized vinyl esters have been completely or partially hydrolyzed,
   g) 0 to 70% by weight of at least one pigment,
   h) 0.5 to 15% by weight of a finely divided crospovidone with an average particle diameter between 2 and 30 micrometers, and
   i) 0 to 30% by weight of further customary auxiliaries,
where the constituents f) to i) add up to 100% by weight.

16. The dosage form according to claim 1, wherein the film coating C) consists of
   f) 20 to 70% by weight of a rapidly water-soluble polyether-vinyl ester graft polymer of polyether and vinyl ester, where the polymerized vinyl esters have been completely or partially hydrolyzed,
   g) 0 to 70% by weight of at least one pigment,
   h) 0 to 30% by weight of a finely divided crospovidone with an average particle diameter between 2 and 30 micrometers, and
   i) 0.5 to 20% by weight of further customary auxiliaries,
where the constituents f) to i) add up to 100% by weight.

17. The dosage form according to claim 1, wherein the film coating C) consists of
   f) 20 to 70% by weight of a rapidly water-soluble polyether-vinyl ester graft polymer of polyether and vinyl ester, where the polymerized vinyl esters have been completely or partially hydrolyzed,
   g) 10 to 70% by weight of at least one pigment,
   h) 0 to 30% by weight of a finely divided crospovidone with an average particle diameter between 2 and 30 micrometers, and
   i) 0.5 to 20% by weight of further customary auxiliaries,
where the constituents f) to i) add up to 100% by weight.

18. The dosage form according to claim 1, wherein the dosage form disintegrates in an aqueous medium within 45 seconds.

19. The dosage form according to claim 1, wherein the dosage form disintegrates in an aqueous medium of a mouth within 45 seconds.

20. The dosage form according to claim 1, wherein in a phosphate buffer having a pH of 7.2 at a temperature of 37° C., the dosage form disintegrates within 45 seconds.

* * * * *